(12) United States Patent
Lee et al.

(10) Patent No.: US 9,972,788 B2
(45) Date of Patent: May 15, 2018

(54) FUSED POLYCYCLIC HETEROAROMATIC COMPOUND, ORGANIC THIN FILM INCLUDING COMPOUND AND ELECTRONIC DEVICE INCLUDING ORGANIC THIN FILM

(71) Applicant: Samsung Electronics Co., Ltd., Suwon-si, Gyeonggi-do (KR)

(72) Inventors: Eun Kyung Lee, Seoul (KR); Jeong Il Park, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days. days.

(21) Appl. No.: 15/172,875

(22) Filed: Jun. 3, 2016

(65) Prior Publication Data

US 2017/0104164 A1    Apr. 13, 2017

(30) Foreign Application Priority Data

Oct. 12, 2015   (KR) .......................... 10-2015-0142418

(51) Int. Cl.
*H01L 51/00* (2006.01)
*C07D 495/22* (2006.01)
*H01L 51/05* (2006.01)

(52) U.S. Cl.
CPC ........ *H01L 51/0071* (2013.01); *C07D 495/22* (2013.01); *H01L 51/0541* (2013.01); *H01L 51/0545* (2013.01); *H01L 51/0558* (2013.01)

(58) Field of Classification Search
CPC ..................................................... H01L 51/00
See application file for complete search history.

(56) References Cited

U.S. PATENT DOCUMENTS

| | | | |
|---|---|---|---|
| 7,816,673 B2 | 10/2010 | Park | |
| 2010/0065826 A1 | 3/2010 | Takimiya et al. | |
| 2013/0116447 A1 | 5/2013 | Park et al. | |
| 2014/0187792 A1 | 7/2014 | Ikeda et al. | |

FOREIGN PATENT DOCUMENTS

| | | |
|---|---|---|
| JP | 2009/054809 A | 3/2009 |
| KR | 2014/0060489 A | 5/2014 |
| WO | WO-2008/050726 A1 | 5/2008 |
| WO | WO-2009/009790 A1 | 1/2009 |

*Primary Examiner* — Paul V Ward
(74) *Attorney, Agent, or Firm* — Harness, Dickey & Pierce, P.L.C.

(57) ABSTRACT

A fused polycyclic heteroaromatic compound is represented by one of Chemical Formula 1, 2A and 2B.

8 Claims, 3 Drawing Sheets

FUSED POLYCYCLIC HETEROAROMATIC COMPOUND, ORGANIC THIN FILM INCLUDING COMPOUND AND ELECTRONIC DEVICE INCLUDING ORGANIC THIN FILM

CROSS-REFERENCE TO RELATED APPLICATION

This application claims priority to and the benefit of Korean Patent Application No. 10-2015-0142418 filed in the Korean Intellectual Property Office on Oct. 12, 2015, the entire contents of which are incorporated herein by reference.

BACKGROUND

1. Field

Example embodiments relate to a fused polycyclic heteroaromatic compound, an organic thin film including the same, and an electronic device including the organic thin film.

2. Description of the Related Art

Flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, there has been research on a low-molecular-weight organic material, e.g., pentacene, or a polymer organic material, e.g., polythiophene, as an organic semiconductor material to be used for a channel of a thin film transistor.

However, the polymer organic material has lower charge mobility and a higher off-state leakage current. On the other hand, the low-molecular-weight organic material, for example, pentacene is reported to have higher charge mobility of greater than or equal to about 3.2 to about 5.0 cm$^2$/Vs but needs expensive vacuum deposition equipment to form a thin film, and thus may not be appropriate in terms of processability and formation of a larger area.

Accordingly, development of a new organic semiconductor material simultaneously having improved electrical characteristics and processability is continuously required.

SUMMARY

Example embodiments provide a relatively low-molecular-weight fused polycyclic heteroaromatic compound that has a compact planar structure in which aromatic rings are fused together and that includes nitrogen at an outmost aromatic ring and/or in a center aromatic ring, and thereby exhibits relatively high charge mobility, and furthermore, enables the use of a deposition process or a room-temperature (about 20° C. to about 25° C.) solution process when applied to devices, therefore realizing improved processability.

Example embodiments also provide an organic thin film including the fused polycyclic heteroaromatic compound.

Example embodiments also provide an electronic device including the organic thin film as a carrier transport layer.

According to example embodiments, a fused polycyclic heteroaromatic compound is represented by Chemical Formula 1.

[Chemical Formula 1]

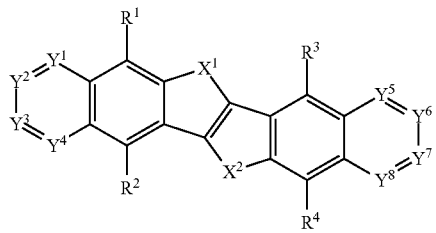

In Chemical Formula 1,
each of $X^1$ and $X^2$ is independently one of S, Se, and Te,
each of $Y^1$ to $Y^8$ is independently one of nitrogen (N) and C—$R^a$, wherein $R^a$ is one of hydrogen and a linear or branched $C_1$ to $C_{10}$ alkyl group, provided that at least one of $Y^1$ to $Y^4$ and at least one of $Y^5$ to $Y^8$ are nitrogen, and
each of $R^1$ to $R^4$ is independently one of hydrogen, a substituted or unsubstituted $C_1$ to $C_{30}$ alkyl group, a substituted or unsubstituted $C_6$ to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

In Chemical Formula 1, at least one of $Y^1$ to $Y^4$ may be a first nitrogen and at least one of $Y^5$ to $Y^8$ may be a second nitrogen, and the first nitrogen and the second nitrogen may be facing each other.

In Chemical Formula 1, at least two of $Y^1$ to $Y^4$ may be nitrogen and at least two of $Y^5$ to $Y^8$ may be nitrogen.

The fused polycyclic heteroaromatic compound may have a molecular weight of about 300 to about 3000.

The fused polycyclic heteroaromatic compound represented by Chemical Formula 1 may include, for example, at least one of compounds (1) to (8) represented by Chemical Formula 1-1.

[Chemical Formula 1-1]

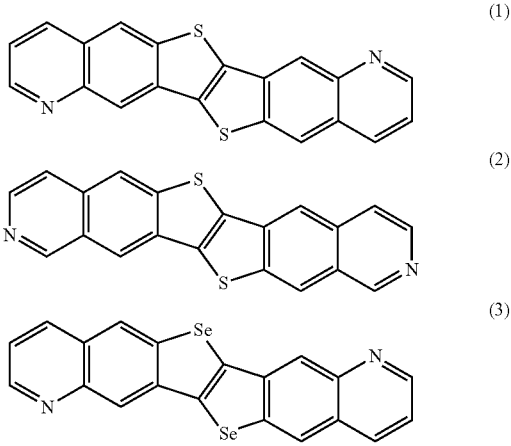

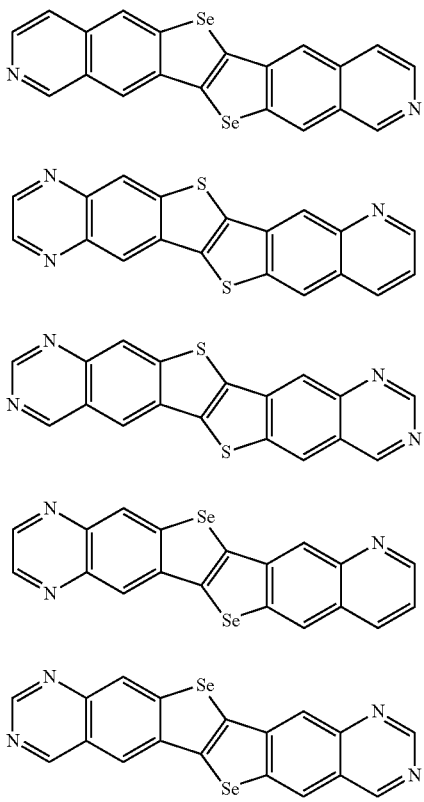

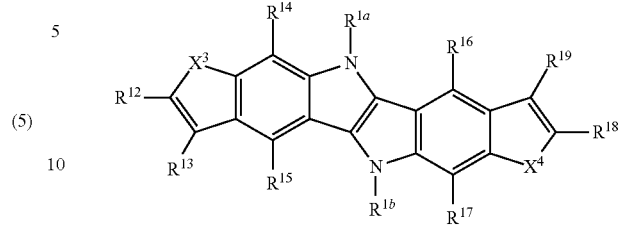

In Chemical Formula 1-1, a hydrogen of each aromatic ring may be replaced by a substituent, for example a substituted or unsubstituted $C_1$ to $C_{30}$ linear or branched alkyl group, a substituted or unsubstituted $C_6$ to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

According to example embodiments, a fused polycyclic heteroaromatic compound is represented by one of Chemical Formula 2A and 2B.

[Chemical Formula 2A]

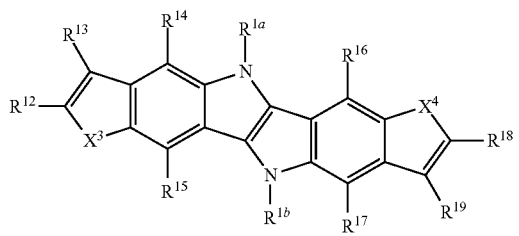

[Chemical Formula 2B]

In Chemical Formulae 2A and 2B, each of $X^3$ and $X^4$ is independently one of S, Se, and Te, each of $R^{1a}$ and $R^{1b}$ is independently one of hydrogen and a linear or branched $C_1$ to $C_{10}$ alkyl group, and each of $R^{12}$ to $R^{19}$ is independently one of hydrogen, a substituted or unsubstituted $C_1$ to $C_{30}$ alkyl group, a substituted or unsubstituted $C_6$ to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

The fused polycyclic heteroaromatic compound represented by Chemical Formula 2A or 2B may include at least one of compounds (9) to (12) represented by Chemical Formula 2-1.

[Chemical Formula 2-1]

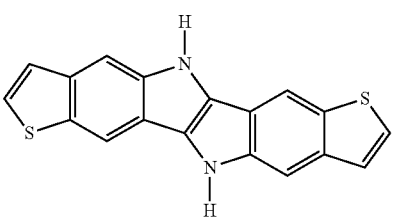

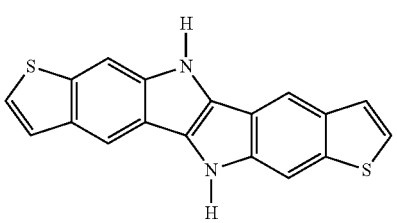

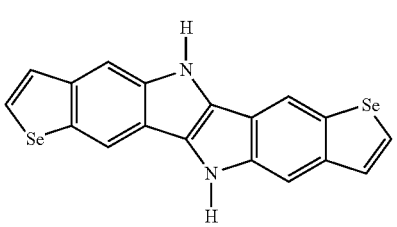

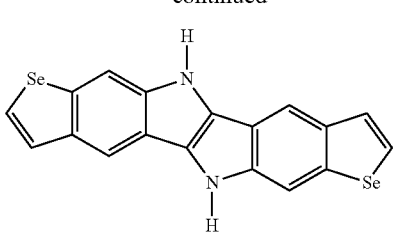

(12)

In Chemical Formula 2-1, hydrogen of each aromatic ring may be replaced by a substituent, for example one of a substituted or unsubstituted $C_1$ to $C_{30}$ linear or branched alkyl group, a substituted or unsubstituted $C_6$ to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

According to example embodiments, an organic thin film and an electronic device include the fused polycyclic heteroaromatic compound.

The electronic device may be one of a transistor, an organic light emitting diode (OLED), a photovoltaic device, a solar cell, a laser device, a memory device, and a sensor.

DETAILED DESCRIPTION

Figure 1:
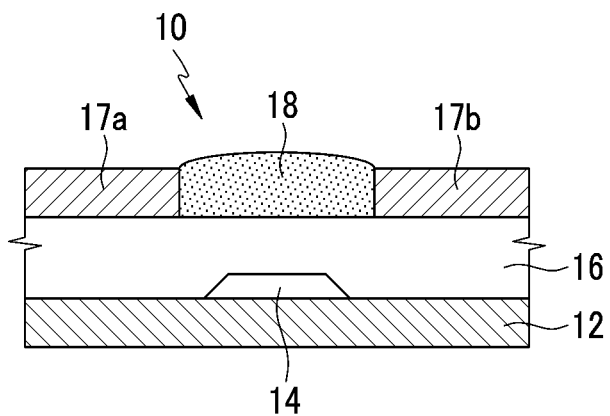
FIG. 1 is a schematic cross-sectional view showing a transistor according to example embodiments.

The present disclosure will be described more fully hereinafter with reference to the accompanying drawings, in which example embodiments are shown. However, this disclosure may be embodied in many different forms and is not construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, the term "combination thereof" refers to a mutual substituent, a mixture, a stacked structure, etc.

As used herein, when a definition is not otherwise provided, the prefix "hetero" may refer to a group that includes 1 to 4 heteroatoms, each independently one of N, O, S, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. Heterocycloalkyl groups include at least one non-aromatic ring that contains a heteroatom ring member. Heteroaryl groups include at least one aromatic ring that contains a heteroatom ring member. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, etc).

The term "aryl group" may refer to a monovalent functional group formed by the removal of one hydrogen atom from a ring of an arene, e.g., phenyl or naphthyl. The arene may refer to a hydrocarbon having an aromatic ring, and includes monocyclic and polycyclic hydrocarbons, wherein the additional ring(s) of the polycyclic hydrocarbon may be aromatic or nonaromatic.

The "arylalkyl group" may refer to aryl group where at least one hydrogen atom is substituted with a lower alkylene, e.g., methylene, ethylene, propylene, etc. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "heteroarylalkyl group" may refer to the alkyl group defined above where at least one hydrogen atom is substituted with a heteroaryl group.

The term "alkylheteroaryl group" may refer to the heteroaryl group defined above, where at least one hydrogen atom is substituted with alkyl group.

As used herein, when a definition is not otherwise provided, the term "aromatic ring" refers to a functional group in which all atoms in the cyclic functional group have a p-orbital, and wherein these p-orbitals are conjugated. For example, the aromatic ring may be a $C_6$ to $C_{20}$ aryl group.

As used herein, when a definition is not otherwise provided, the term "substituted" means that a compound or group is substituted with at least one substituent independently selected from a halogen (—F, —Cl, —Br, or —I), a $C_1$ to $C_{30}$ linear or branched alkyl group, for example a $C_1$ to $C_{10}$ linear or branched alkyl group, a $C_2$ to $C_{30}$ linear or branched alkenyl group, for example a $C_2$ to $C_{10}$ linear or branched alkenyl group, a $C_2$ to $C_{30}$ linear or branched alkynyl group, for example a $C_2$ to $C_{10}$ linear or branched alkynyl group, a $C_6$ to $C_{30}$ aryl group, for example a $C_6$ to $C_{12}$ aryl group, a $C_2$ to $C_{30}$ heteroaryl group, for example a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($C_nF_{2n+1}$), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group (—NRR', wherein each of R and R' is independently one of hydrogen or a $C_1$ to $C_{10}$ alkyl group), an amidino group (—C(=NH)NH$_2$), a nitro group (—NO$_2$), an amide group (—C(=O)NHR, wherein R is hydrogen or a $C_1$ to $C_{10}$ alkyl group), an aldehyde group (—C(=O)H), a hydroxy group (—OH), a sulfonyl group (—S(=O)$_2$R, wherein R is independently hydrogen or a $C_1$ to $C_{10}$ alkyl group), and a carbamate group (—NHC(=O)OR, wherein R is a $C_1$ to $C_{10}$ alkyl group), instead of hydrogen of the functional group or the compound, provided that the substituted atom's normal valence is not exceeded.

According to example embodiments, a fused polycyclic heteroaromatic compound is represented by Chemical Formula 1 and has a compact planar structure in which a 5-membered or 6-membered aromatic ring are fused together.

[Chemical Formula 1]

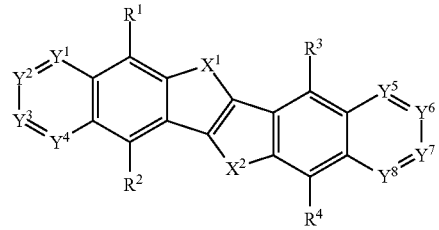

In Chemical Formula 1,
each of $X^1$ and $X^2$ is independently one of S, Se, and Te,
each of $Y^1$ to $Y^8$ is independently one of nitrogen (N) and C—$R^a$, wherein $R^a$ is one of hydrogen and a linear or branched $C_1$ to $C_{10}$ alkyl group, provided that at least one of $Y^1$ to $Y^4$ and at least one of $Y^5$ to $Y^8$ are nitrogen, and
each of R' to $R^4$ is independently one of hydrogen, a substituted or unsubstituted $C_1$ to $C_{30}$ alkyl group, a substituted or unsubstituted C6 to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

In Chemical Formula 1, at least one of $Y^1$ to $Y^4$ may be nitrogen (first nitrogen) and at least one of $Y^5$ to $Y^8$ may be nitrogen (second nitrogen), and the first nitrogen and the second nitrogen may be positioned facing each other.

In Chemical Formula 1, at least two of $Y^1$ to $Y^4$ may be nitrogen and at least two of $Y^5$ to $Y^8$ may be nitrogen. For example, an aromatic ring present at the outmost may be a pyrimidine ring or a pyrazine ring.

The fused polycyclic heteroaromatic compound represented by Chemical Formula 1 has a structure that six rings including aromatic rings and hetero aromatic rings are fused, of which the outmost aromatic ring contains nitrogen. The nitrogen-containing aromatic ring may increase a molecular arrangement through a hydrogen bond among molecules, have an advantage of packing and stacking the molecules, and resultantly show relatively high charge mobility. When the molecular arrangement is increased as above, a given or predetermined molecular arrangement of the compound may be induced during formation of a thin film through a deposition process, and thus thin film uniformity may be improved.

In addition, the fused polycyclic heteroaromatic compound is easily synthesized to be effectively applied to a semiconductor material, an electron transporting material, etc. By having a compact planar molecular structure in which six aromatic rings and hetero aromatic rings are fused, oxidation potentials are relatively uniform and stable when the fused polycyclic heteroaromatic compound is applied to an actual device.

The fused polycyclic heteroaromatic compound represented by Chemical Formula 1 may have a hydrogen bond by including a hetero atom selected from S, Se, and Te present in a core aromatic ring and at least one N in the outmost aromatic ring and thus improve a molecular interaction and provide an advantageous packing structure for a charge transfer. In addition, the fused polycyclic heteroaromatic compound may have improved thermal stability and thus improve heat resistance of a device.

The fused polycyclic heteroaromatic compound represented by Chemical Formula 1 may include, for example, at least one of compounds (1) to (8) represented by Chemical Formula 1-1.

[Chemical Formula 1-1]

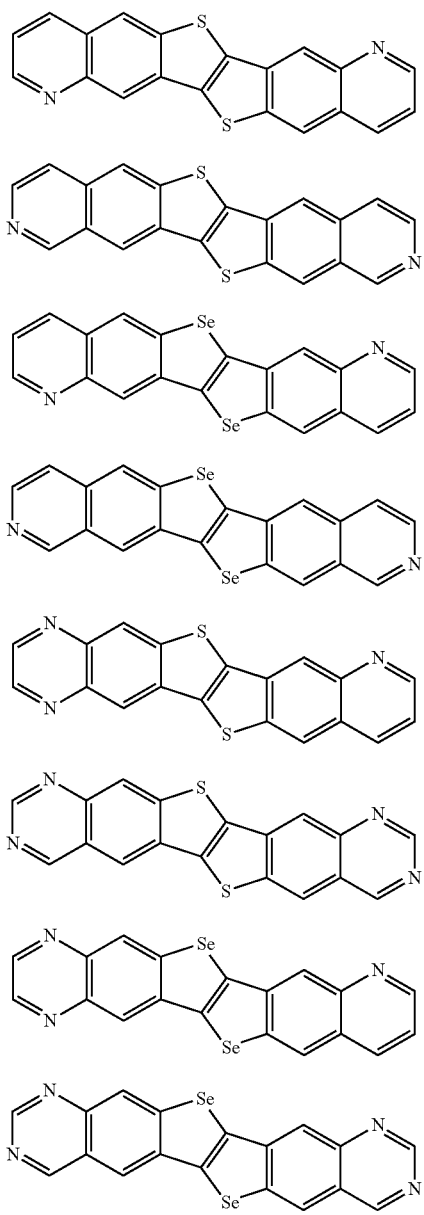

In Chemical Formula 1-1,
hydrogen of each aromatic ring may be replaced by a substituent, for example a substituted or unsubstituted $C_1$ to $C_{30}$ linear or branched alkyl group, a substituted or unsubstituted C6 to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

According to example embodiments, a fused polycyclic heteroaromatic compound is represented by one of Chemical Formula 2A and 2B.

[Chemical Formula 2A]

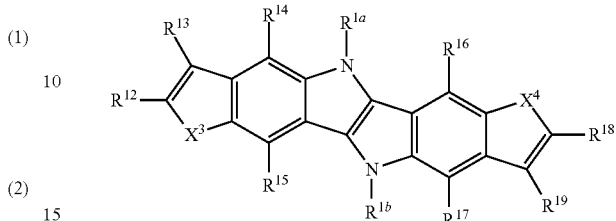

[Chemical Formula 2B]

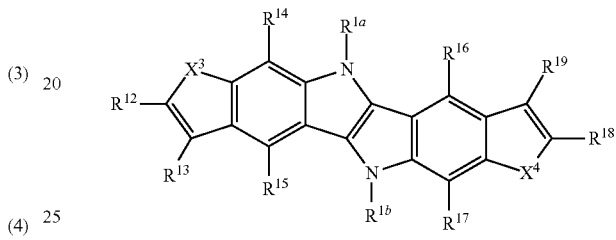

In Chemical Formulae 2A and 2B,
each of $X^3$ and $X^4$ is independently one of S, Se, and Te,
each of $R^{1a}$ and $R^{1b}$ is independently one of hydrogen and a linear or branched $C_1$ to $C_{10}$ alkyl group, and
each of $R^{12}$ to $R^{19}$ is independently one of hydrogen, a substituted or unsubstituted $C_1$ to $C_{30}$ alkyl group, a substituted or unsubstituted C6 to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

The fused polycyclic heteroaromatic compound represented by Chemical Formula 2A or 2B has a structure that six rings of aromatic rings and hetero aromatic ring are fused, of which the core aromatic ring contains nitrogen. The nitrogen-containing aromatic ring may increase a molecular arrangement through a hydrogen bond among molecules and thus have an advantage of packing and stacking the molecules and resultantly, show high charge mobility. When the molecular arrangement is increased as above, a constant molecular arrangement of the compound may be induced during formation of a thin film through a deposition process, and thin film uniformity may be improved.

In addition, the fused polycyclic heteroaromatic compound is easily synthesized to be effectively applied to a semiconductor material, an electron transporting material, etc. By having a compact planar molecular structure in which six aromatic rings and hetero aromatic rings are fused, oxidation potentials are relatively uniform and stable when the fused polycyclic heteroaromatic compound is applied to an actual device.

The fused polycyclic heteroaromatic compound represented by Chemical Formula 2A or 2B may have a hydrogen bond by including N in the core aromatic ring and a hetero atom selected from S, Se, and Te in the outmost aromatic ring and thus improve a molecular interaction and provide an advantageous packing structure for a charge transfer. In addition, the fused polycyclic heteroaromatic compound has improved thermal stability and may improve heat resistance of a device.

The fused polycyclic heteroaromatic compound represented by Chemical Formula 2A or 2B may include at least one of compounds (9) to (12) represented by Chemical Formula 2-1.

[Chemical Formula 2-1]

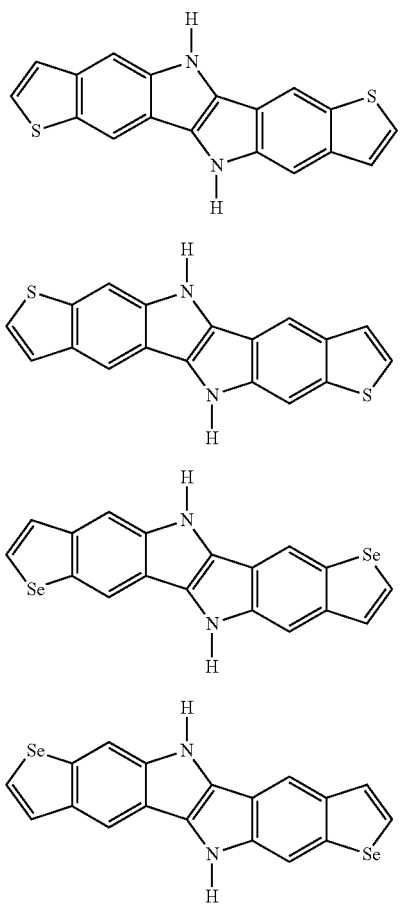

In Chemical Formula 2-1, a hydrogen of each aromatic ring may be replaced by a substituent, for example a substituted or unsubstituted $C_1$ to $C_{30}$ linear or branched alkyl group, a substituted or unsubstituted C6 to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

The HOMO energy, reorganization energy, and expectation mobility of compounds of compound (1) and compound (2) of the fused polycyclic heteroaromatic compound are calculated, and the results are shown in Table 1. The HOMO energy and the reorganization energy are calculated by using a Gaussian 09 program in DFT B3LYP/6-31G (d, p) level, and a transfer integral is calculated by using the ADF (Amsterdam Density Functional) program at PW91-TZP, to calculate expectation mobility according to Marcus theory. For comparison, the HOMO energy, reorganization energy, and expectation mobility of compounds of ref-1 and ref-2 are also shown in Table 1.

TABLE 1

| Compounds | $E_{HOMO}$ (eV) | Reorganization energy (meV) | Expectation mobility (rel.) (cm$^2$/Vs) |
|---|---|---|---|
| compound ref-1 | −5.57 | 146 | 0.9 |
| compound ref-2 | −5.59 | 218 | 0.14 |
| compound (1) | −5.77 | 149 | 1.5 |
| compound (2) | −5.90 | 153 | 1.6 |

As shown in Table 1, the compounds (1) and (2) have smaller reorganization energy compared with the compounds ref-1 and ref-2, and thus charges may be effectively transported among molecules. The compounds (1) and (2) exhibit higher expectation mobility compared with the compounds ref-1 and ref-2.

The fused polycyclic heteroaromatic compound according to example embodiments may have a molecular weight of about 300 to about 3000, for example 300 to 1000. Within the range of the average molecular weight, the fused polycyclic heteroaromatic compound may be relatively easy to handle.

The fused polycyclic heteroaromatic compound may be prepared according to a general method, for example, chemical or electrochemical oxidation synthesis, which is a representative method of polymerizing an aromatic compound or a heteroaromatic compound, or condensation polymerization using a compound of an organic transition element, e.g., nickel or palladium.

Example embodiments provide an organic thin film including the fused polycyclic heteroaromatic compound and an electronic device including the organic thin film.

The organic thin film according to example embodiments includes the aforementioned fused polycyclic heteroaromatic compound, and thus may be used as an organic semiconductor layer for an electronic device and a carrier transport layer, e.g., a channel layer, and the electronic device including the organic thin film shows improved electrical characteristics with high charge mobility as well as improved processability and workability.

Herein, the organic thin film may be manufactured by depositing more than one kind of the fused polycyclic heteroaromatic compound on a substrate in a common method or dissolving the fused polycyclic heteroaromatic compound in an organic solvent and coating the solution in a common room temperature solution process, and the deposited or coated thin film may be heat-treated to increase density and uniformity thereof.

Particularly, the organic solvent may include at least one kind of general organic solvent, for example, at least one kind of an aliphatic hydrocarbon solvent (e.g., hexane and/or heptane); an aromatic hydrocarbon solvent (e.g., toluene, pyridine, quinoline, anisole, mesitylene and/or xylene); a ketone-based solvent (e.g., methyl isobutyl ketone, 1-methyl-2-pyrrolidinone, cyclohexanone and/or acetone); an ether-based solvent (e.g., tetrahydrofuran and/or isopropyl ether); an acetate-based solvent (e.g., ethyl acetate, butyl acetate and/or propylene glycol methyl ether acetate); an alcohol-based solvent (e.g., isopropyl alcohol and/or butanol); an amide-based solvent (e.g., dimethyl acetamide and/or dimethyl formamide); a silicone-based solvent; and a mixture of solvents. The amount of the fused polycyclic heteroaromatic compound dissolved in the organic solvent may be appropriately selected and determined by a person of ordinary skill in the art, for example, in a range of about 0.01 wt % to about 50 wt % based on the total solution in view of solubility and coating property.

The method of providing an organic thin film may include thermal deposition, vacuum deposition, laser deposition, screen printing, printing, imprinting, spin casting, dipping, ink jetting, roll coating, flow coating, drop casting, spray coating, and/or roll printing, but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent by a person of ordinary skill in the art, and is specifically in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, and/or a sensor, and the organic thin film may be applied to each device according to the general process commonly known in the art.

For example, the transistor includes a gate electrode disposed on a substrate, a source electrode and a drain electrode facing each other and defining a channel region, an insulation layer electrically insulating the source electrode and drain electrode and the gate electrode, and an active layer including the fused polycyclic heteroaromatic compound formed in the channel region.

The active layer may be obtained by depositing the fused polycyclic heteroaromatic compound, or applying a composition including the fused polycyclic heteroaromatic compound to a solution process, for example, screen printing, printing, spin coating, dipping, and/or ink jetting. When the active layer is formed by the solution process, the process cost may be reduced, and a large area device may be effectively manufactured.

Figure 2:
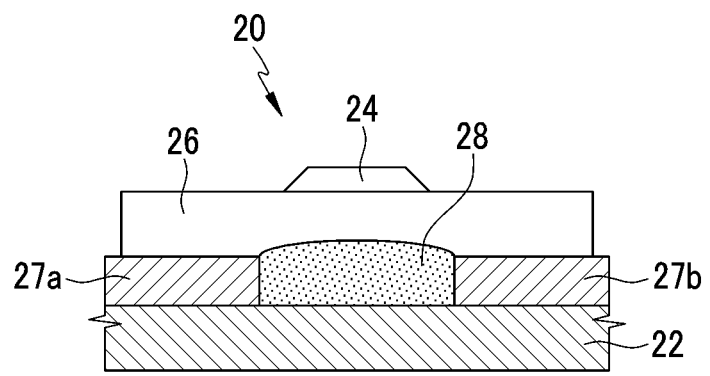
FIG. 2 is a schematic cross-sectional view showing a transistor according to example embodiments.

FIGS. 1 and 2 are schematic cross-sectional views showing a transistor according to example embodiments. The transistor according to example embodiments may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. A source electrode 17a and a drain electrode 17b defining a channel region are provided on the insulation layer 16, and an active layer 18 is provided in the channel region. The active layer 18 includes the fused polycyclic heteroaromatic compound.

Referring to FIG. 2, a transistor 20 includes a source electrode 27a and a drain electrode 27b defining a channel region and that are formed on a substrate 22, and an active layer 28 formed on the channel region. The active layer 28 includes the fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic (e.g., polyethylene naphthalate (PEN), polyethylene terephthalate (PET), polycarbonate, polyvinyl alcohol, polyacrylate, polyimide, polynorbornene, and polyethersulfone (PES)), and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but is not limited thereto.

The insulation layers 16 and 26 may include a generally-used insulator having a high dielectric constant, for example, a ferroelectric insulator (e.g., $Ba_{0.33}Sr_{0.66}TiO_3$ (BST, barium strontium titanate), $Al_2O_3$, $Ta_2O_5$, $La_2O_5$, $Y_2O_3$ and/or $TiO_2$); an inorganic insulator (e.g., $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_x$ (x is determined depending on valence of Si), and/or AlON (aluminum oxynitride)); or an organic insulator (e.g., polyimide, benzocyclobutane (BCB), parylene, polyacrylate, polyvinyl alcohol, and polyvinylphenol), but is not limited thereto.

Hereinafter, the embodiments are illustrated in more detail with reference to examples. However, these are examples, and the present disclosure is not limited thereto.

Example 1: Synthesis of Compound (1)

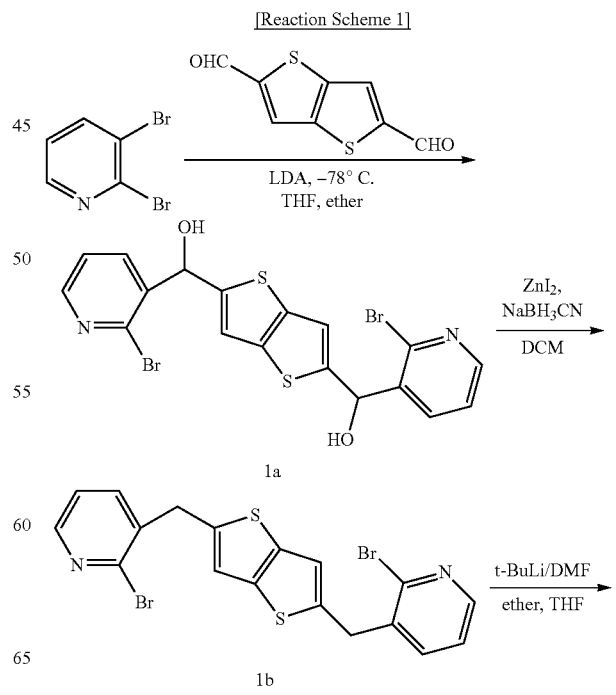

[Reaction Scheme 1]

-continued

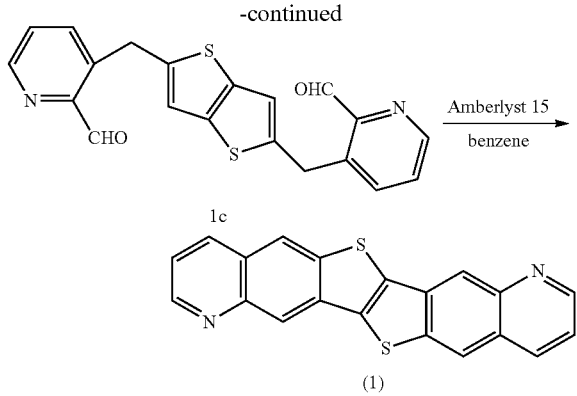

(1) Synthesis of Thieno[3,2,b]thiophene-2,5-diylbis ((2-bromopyridin-3-yl)methanol (Compound 1a)

Thienothiophene dicarbaldehyde (5 g, 25.48 mmol) is dissolved in 250 mL of dry diethylether and dry tetrahydrofuran and then, cooled down to −78° C. 42.12 mL of lithium diisopropylamine (a 2.0 M hexane solution) is slowly added thereto in a dropwise fashion, and 2,3-dibromopyridine (13.3 g, 56.16 mmol) is added thereto. The temperature is slowly increased, and the mixture is stirred at room temperature (24° C.) for 12 hours. Then, 100 mL of an ammonium chloride-saturated solution is added thereto, and an extract is obtained by using chloroform and several times washed with water. The extract is dried with magnesium sulfate and filtered, and the chloroform solvent is removed to obtain a compound 1a. (a yield of 75%)

(2) Synthesis of 2,5-bis(2-bromopyridin-3-yl) methyl)thieno[3,2,b]thiophene (Compound 1b)

The compound 1a (9.8 g, 19.13 mmol) is dissolved in 300 mL of dichloromethane, and $ZnI_2$ (19.54 g, 61.22 mmol) and $NaCNBH_3$ (16.83 g, 267.8 mmol) are slowly added thereto. The mixture is stirred at room temperature (24° C.) for 24 hours and passed through a Celite pad. The filtered solution is respectively washed with an ammonium chloride saturated solution and water, dried with $MgSO_4$, and concentrated under a reduced pressure to obtain yellow oil. This obtained material is purified through silica chromatography, obtaining a desired compound 1b. (a yield of 80%)

(3) Synthesis of 3,3'-(thieno[3,2,b]thiophen-2,5-diylbis(methylene))dipicolinealdehyde (Compound 1c)

A tetrahydrofuran solution (100 mL) in which the compound 1b (5.7 g, 11.13 mmol) is dissolved is added in a dropwise fashion to the diethyl ether (200 mL) solution in which t-butyl lithium (30.11 mmol) is dissolved and cooled down to −78° C. The mixed solution is stirred at −78° C. for about 30 minutes, dimethylformaldehyde (2.44 g) is added thereto, and the obtained mixture is stirred for about 2 hours again. When the reaction is completed by pouring water thereinto, 200 mL of ethyl acetate is added thereto, the mixture is washed with water and brine, and an organic layer produced therein is dried with $MgSO_4$ and concentrated under a reduced pressure, obtaining colorless oil. This obtained material is purified through silica chromatography, obtaining a desired compound 1c (a yield of 50%).

(4) Synthesis of Compound (1)

30 mL of the compound 1c (2.1 g) is dissolved in benzene, Amberlyst 15 (0.5 g) is added thereto, and water is removed therefrom by using a Dean-Stark trap while the mixture is stirred and refluxed. After 24 hours, a yellow solid is precipitated. The temperature is cooled down to room temperature (24° C.), the Amberlyst 15 is precipitated and then, filtered after taking off a floater therefrom, obtained a desired compound 1 as a yellow solid (a yield of 60%).

Figure 3:
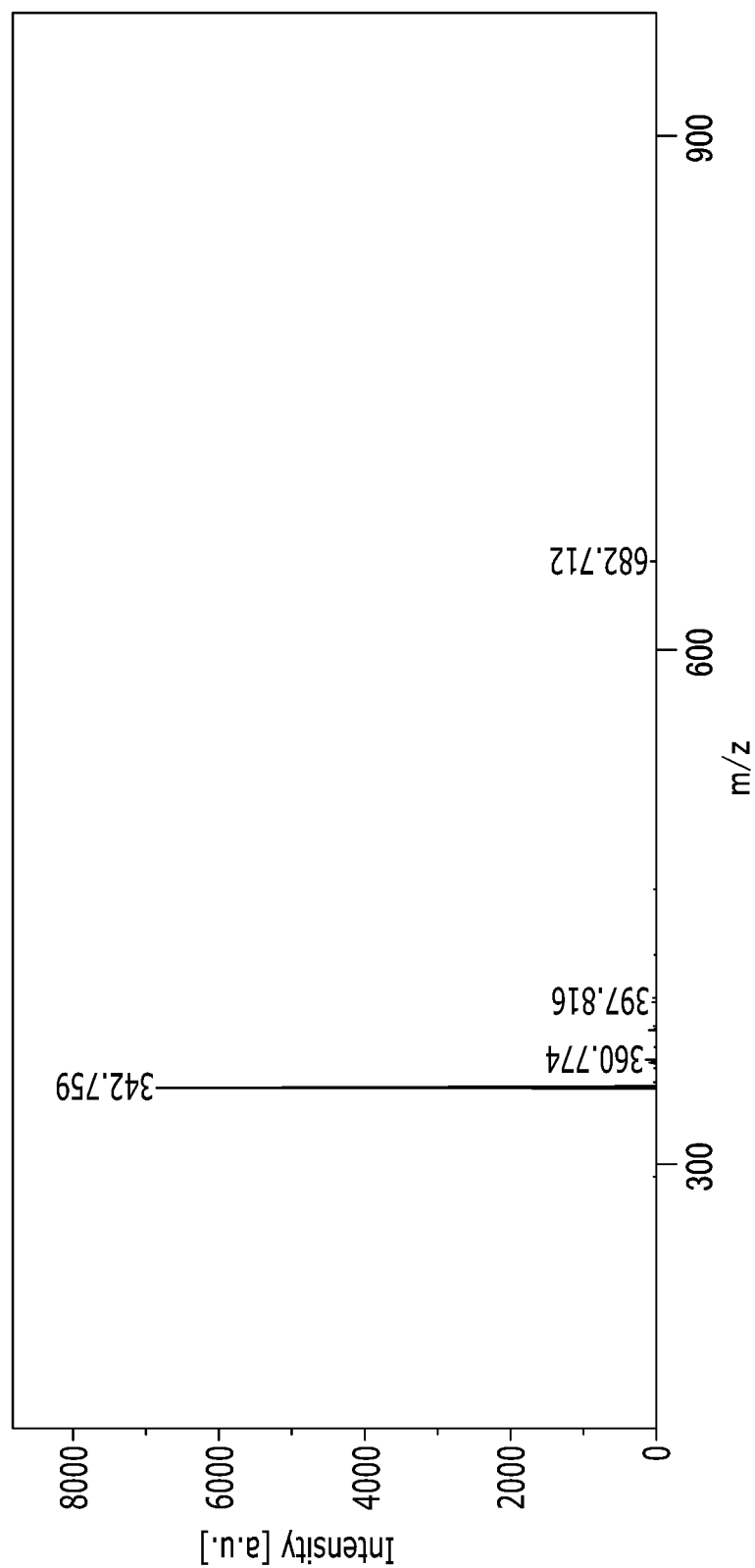
FIG. 3 shows a MALDI-MS analysis result of the compound (1) synthesized according to Example 1.

The MALDI-MS analysis result of the compound 1 is provided in FIG. 3.

Maldi-MS m/z=342.76 (M+1).

Example 2: Synthesis of Compound (2)

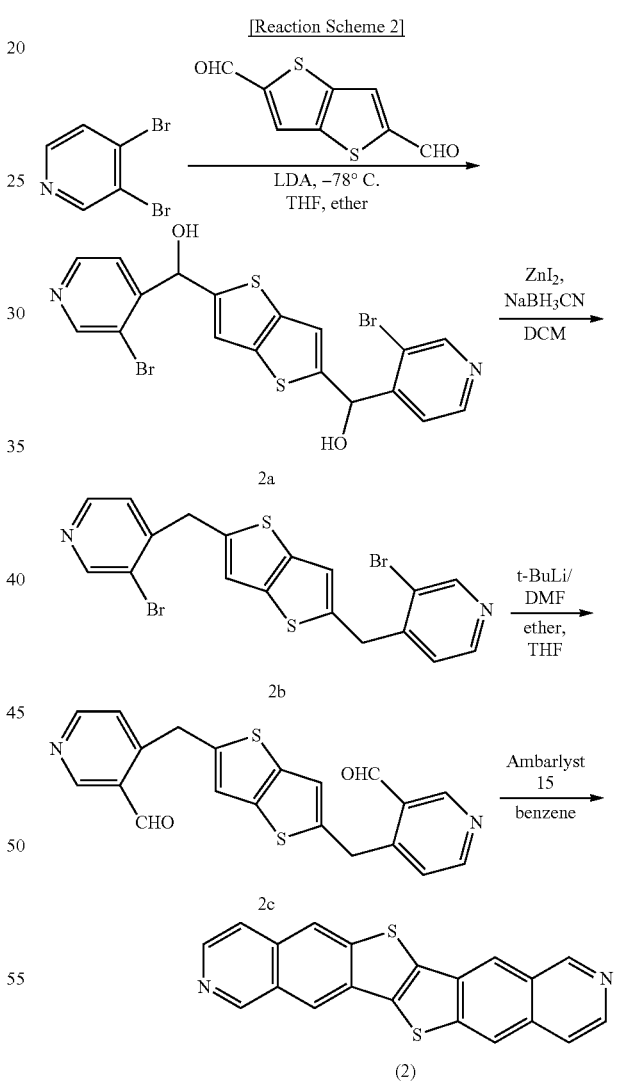

(1) Synthesis of Thieno[3,2,b]thiophene-2,5-diylbis ((3-bromopyridin-3-yl)methanol (Compound 2a)

Thienothiophene dicarbaldehyde (5 g, 25.48 mmol) is dissolved in 250 mL of dry diethylether and dry tetrahydrofuran (THF) and then, cooled down to −78° C. Then, 42.12 mL of diisopropylamine (a 2.0 M hexane solution) is slowly added thereto in a dropwise fashion, and 2,3-dibromopyridine (13.3 g, 56.16 mmol) is added thereto. The mixture is slowly heated and stirred at room temperature (24° C.) for 12 hours. Subsequently, 100 mL of an ammonium chloride-saturated solution is added thereto, and an extract is obtained by using chloroform and several times washed with water. The obtained extract is dried with magnesium sulfate and then, filtered, and the chloroform solvent is removed to obtain a compound 2a. (a yield of 75%)

(2) Synthesis of 2,5-bis(3-bromopyridin-3-yl)methyl)thieno[3,2,b]thiophene (Compound 2b)

The compound 2a (9.8 g, 19.13 mmol) is dissolved in 300 mL of dichloromethane, and $ZnI_2$ (19.54 g, 61.22 mmol) and $NaCNBH_3$ (16.83 g, 267.8 mmol) are slowly added thereto. The mixture is stirred at room temperature (24° C.) for 24 hours and passed through a Celite pad. The filtered solution is respectively washed with an ammonium chloride-saturated solution and water, dried with $MgSO_4$, and concentrated under a reduced pressure, obtaining yellow oil. This obtained material is purified through silica chromatography, obtaining a desired compound 2b. (a yield of 80%)

(3) Synthesis of 4,4'-(thieno[3,2-b]thiophene-2,5-diylbis(methylene))dinicotinaldehyde (Compound 2c)

A tetrahydrofuran solution (100 mL) in which the compound 2b (5.7 g, 11.13 mmol) is dissolved is slowly added in a dropwise fashion to a diethyl ether (200 mL) solution in which t-butyl lithium (30.11 mmol) is dissolved and cooled down to −78° C. The mixture is stirred at −78° C. for about 30 minutes, dimethylformaldehyde (2.44 g) is added thereto, and the obtained mixture is stirred again for about 2 hours. When the reaction is completed by pouring water thereinto, 200 mL of ethyl acetate is added thereto, the mixture is washed with water and brine, and an organic layer produced therein is dried with $MgSO_4$, and concentrated under a reduced pressure, obtaining colorless oil. This obtained material is purified through silica chromatography, obtaining a desired compound 2c (a yield of 50%).

(4) Synthesis of Compound (2)

The compound 2c (2.1 g) is dissolved in 30 mL of benzene, Amberlyst 15 (0.5 g) is added thereto, and water is removed therefrom by using a Dean-Stark trap while the mixture is stirred and refluxed. After 24 hours or so, a yellow solid is precipitated. The temperature is cooled down to room temperature (24° C.), the Amberlyst 15 is precipitated and then, filtered after taking off a floater therefrom, obtaining a desired compound 2 as a yellow solid (a yield of 60%).

Figure 4:
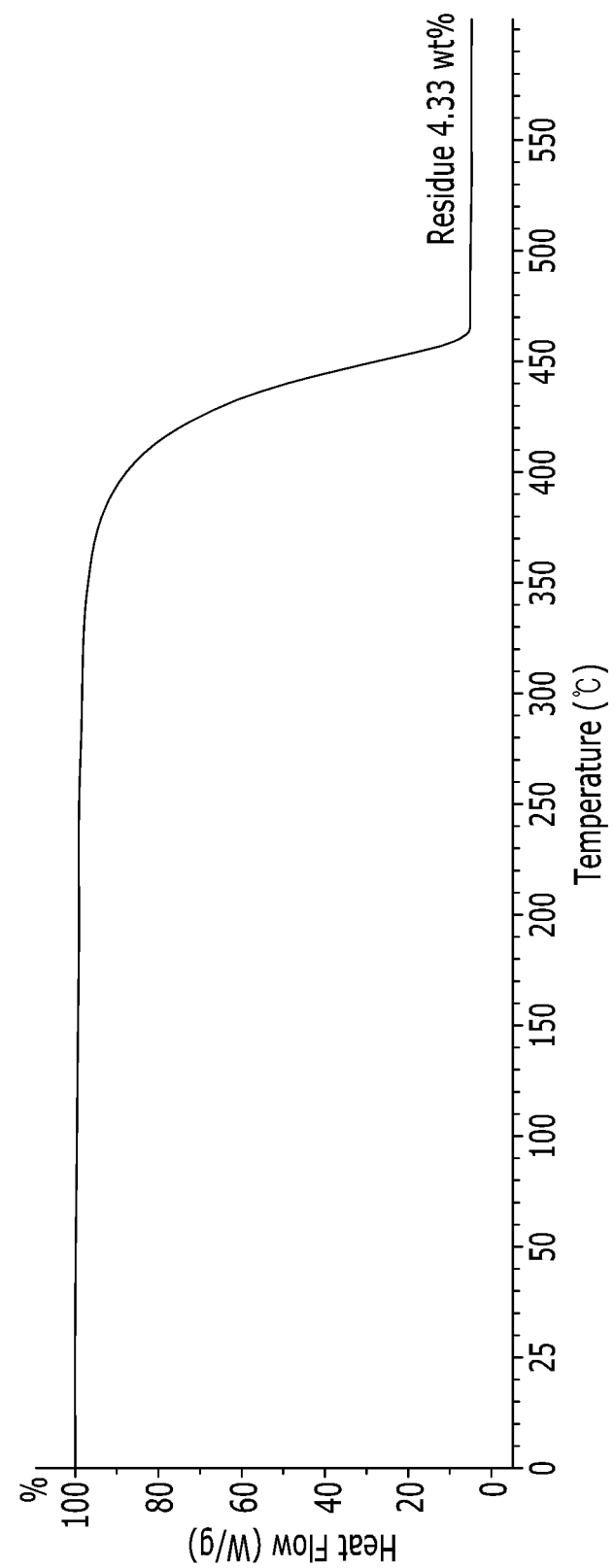
FIG. 4 shows a thermogravimetric analysis result (TGA) of the compound (1) synthesized according to Example 1.

The thermogravimetric analysis result (TGA) of the compound 1 is provided in FIG. 4. As shown in FIG. 4, a temperature when 5 wt % of the compound 1 is decreased is 383.02° C. Accordingly, the compound 1 turns out to have improved thermal stability.

Example 3: Manufacture of Organic Thin Film Transistor (OTFT)

First, chromium used as a gate electrode is deposited to be 1000 Å thick through sputtering on a cleaned glass substrate, and $SiO_2$ is deposited to form a 3000 Å-thick insulation layer thereon in a CVD method. Then, Au is deposited thereon to be 700 Å thick through sputtering, forming a source electrode and a drain electrode. The glass substrate is cleaned with isopropyl alcohol for 10 minutes and dried before coating an organic semiconductor material. In addition, the $SiO_2$ used as an insulation layer is treated with $UV/O_3$ for 30 minutes before surface modification.

Then, an OTFT device 10 having a structure shown in FIG. 1 is manufactured by dipping the substrate in n-hexane and an octyltrichlorosilane solution diluted into a concentration of 10 mM for 30 minutes, washing the substrate with hexane and alcohol, drying the substrate, and thermally evaporating the compound (1) synthesized according to Example 1 under high vacuum ($5 \times 10^{-6}$ torr) at a speed of 0.2 Å/sec to form a 1000 Å-thick active layer 18.

Example 4: Manufacture of Organic Thin Film Transistor (OTFT)

An OTFT device is manufactured according to the same method as in Example 3, except that the compound 2 is used instead of the compound 1.

While this disclosure has been described in connection with what is presently considered to be practical example embodiments, it is to be understood that the present inventive concepts are not limited to the disclosed embodiments, but, on the contrary, is intended to cover various modifications and equivalent arrangements included within the spirit and scope of the appended claims.

What is claimed is:
1. A fused polycyclic heteroaromatic compound represented by Chemical Formula 1:

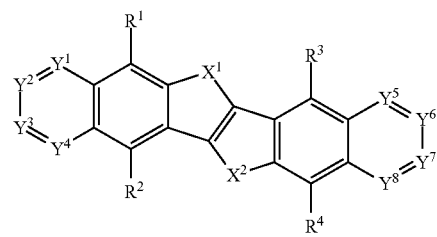

wherein, in Chemical Formula 1,
each of $X^1$ and $X^2$ is independently one of S, Se, and Te,
each of $Y^1$ to $Y^8$ is independently one of nitrogen (N) and C—$R^a$, wherein $R^a$ is one of hydrogen and a linear or branched $C_1$ to $C_{10}$ alkyl group, provided that at least one of $Y^1$ to $Y^4$ and at least one of $Y^5$ to $Y^8$ are nitrogen, and
each of $R^1$ to $R^4$ is independently one of hydrogen, a substituted or unsubstituted $C_1$ to $C_{30}$ alkyl group, a substituted or unsubstituted $C_6$ to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group,
wherein the heteroaryl group includes at least one aromatic ring that contains 1 to 4 heteroatoms in each ring member, and the total number of the ring members is 3 to 10, and the heteroatom include one of N, O, S, Si and P, wherein the heteroarylalkyl group includes an alkyl group where at least one hydrogen atom is substituted with the heteroaryl group, wherein the alkylheteroaryl group includes the heteroaryl group where at least one hydrogen atom is substituted with an alkyl group, wherein the heterocycloalkyl group includes at least one non-aromatic ring that contains 1 to 4 heteroatoms in each ring member, and a total number of the ring members is 3 to 10, and the heteroatom include one of N, O, S, Si and P, and wherein the $R^1$ to $R^4$ groups are "substituted" with a functional group with at least one substituent independently selected from —F, —Cl, —Br, —I, a $C_1$ to $C_{30}$ linear or branched alkyl group, a $C_2$ to $C_{30}$ linear or branched alkenyl group, a $C_2$ to $C_{30}$ linear or branched alkynyl group, a $C_6$ to $C_{30}$ aryl group, a $C_2$ to $C_{30}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($C_nF_{2n+1}$), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group, an amidino group, an aldehyde group, and a carbamate group, instead of hydrogen of the functional group, provided that a substituted atom's normal valence is not exceeded.

2. The fused polycyclic heteroaromatic compound of claim 1, wherein, in Chemical Formula 1, at least one of $Y^1$ to $Y^4$ is a first nitrogen and at least one of $Y^5$ to $Y^8$ is a second nitrogen, wherein, when at least one of $Y^1$ and $Y^4$ is the first nitrogen, at least one of $Y^5$ and $Y^8$ is the second nitrogen, and when at least one of $Y^2$ and $Y^3$ is the first nitrogen, at least one of $Y^6$ and $Y^7$ is the second nitrogen.

3. The fused polycyclic heteroaromatic compound of claim 1, wherein, in Chemical Formula 1, at least two of $Y^1$ to $Y^4$ are nitrogen and at least two of $Y^5$ to $Y^8$ are nitrogen.

4. The fused polycyclic heteroaromatic compound of claim 1, wherein the fused polycyclic heteroaromatic compound has a molecular weight of about 300 to about 3,000.

5. The fused polycyclic heteroaromatic compound of claim 1, wherein the fused polycyclic heteroaromatic compound represented by Chemical Formula 1 includes at least one of compounds (1) to (8) represented by Chemical Formula 1-1:

[Chemical Formula 1-1]

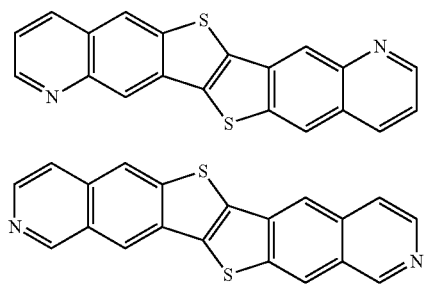

(1)

(2)

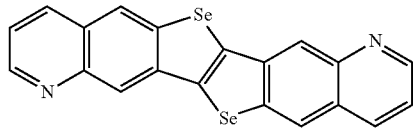

(3)

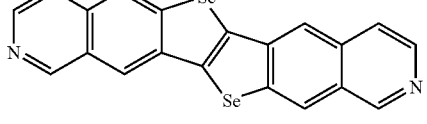

(4)

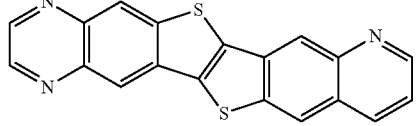

(5)

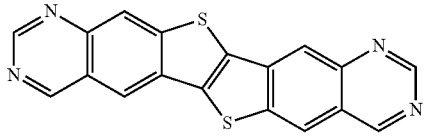

(6)

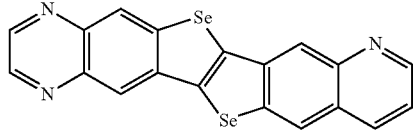

(7)

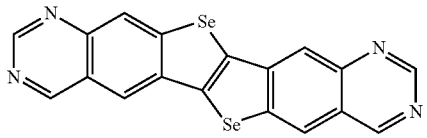

(8)

wherein, in Chemical Formula 1-1, a hydrogen of each aromatic ring is replaced by a substituted or unsubstituted $C_1$ to $C_{30}$ linear or branched alkyl group, a substituted or unsubstituted $C_6$ to $C_{30}$ aryl group and a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

6. An organic thin film comprising the fused polycyclic heteroaromatic compound of claim 1.

7. An electronic device comprising the fused polycyclic heteroaromatic compound of claim 1.

8. The electronic device of claim 7, wherein the electronic device is one of a transistor, an organic light emitting diode (OLED), a photovoltaic device, a solar cell, a laser device, a memory device, and a sensor.

* * * * *